United States Patent
Qi (10) Patent No.: US 9,176,086 B2
(45) Date of Patent: Nov. 3, 2015

(54) FLUID QUALITY SENSING MEANS WITH REFERENCE SENSOR

(71) Applicant: Baohua Qi, Columbus, IN (US)

(72) Inventor: Baohua Qi, Columbus, IN (US)

(*) Notice: Subject to any disclaimer, the term of this patent is extended or adjusted under 35 U.S.C. 154(b) by 182 days.

(21) Appl. No.: 14/025,847

(22) Filed: Sep. 13, 2013

(65) Prior Publication Data

US 2015/0075268 A1    Mar. 19, 2015

(51) Int. Cl.
*G01N 27/22* (2006.01)
*G01N 33/28* (2006.01)
*G01N 27/02* (2006.01)
*F01M 11/10* (2006.01)

(52) U.S. Cl.
CPC ............. *G01N 27/22* (2013.01); *G01N 27/02* (2013.01); *G01N 33/2888* (2013.01); *F01M 2011/14* (2013.01)

(58) Field of Classification Search
CPC .......... F01M 2011/14; G01N 33/2888; G01N 27/002; G01N 27/22
See application file for complete search history.

(56) References Cited

U.S. PATENT DOCUMENTS

| | | | | |
|---|---|---|---|---|
| 3,897,687 A | * | 8/1975 | Burberry ................... | G01N 1/10 73/863.71 |
| 4,646,070 A | * | 2/1987 | Yasuhara et al. ........ | F01M 11/10 324/690 |
| 4,733,556 A | * | 3/1988 | Meitzler et al. ......... | B01D 27/08 340/631 |
| 4,785,287 A | * | 11/1988 | Honma et al. .......... | G01N 29/02 340/631 |
| 5,674,401 A | * | 10/1997 | Dickert et al. ...... | G01N 33/2888 210/695 |
| 6,278,281 B1 | * | 8/2001 | Bauer et al. .......... | G01N 33/2888 324/441 |
| 6,463,796 B1 | * | 10/2002 | Van Mullekom et al. ...................... | F01M 11/04 73/114.55 |
| 7,019,654 B2 | * | 3/2006 | Danyluk et al. ....... | G01N 27/002 340/450.3 |
| 7,493,799 B1 | * | 2/2009 | Discenzo ................ | F16C 19/52 184/108 |
| 7,541,004 B2 | * | 6/2009 | Niksa et al. ........... | G01N 27/126 324/698 |
| 8,643,388 B2 | * | 2/2014 | Hedges .............. | G01N 33/2888 324/698 |
| 2004/0263187 A1 | * | 12/2004 | Hayashi et al. ....... | G01N 27/228 324/698 |

* cited by examiner

*Primary Examiner* — Charlie Y Peng (57) ABSTRACT

A sensing apparatus for detecting fluid quality change using signals obtained from a fluid quality sensor for exposure to a fluid and a reference sensor positioned in a reference sensing means having a fluid trap section holding a part of the fluid. Sensing values obtained from the fluid quality sensor and the reference sensor are compared in determining an aging factor. An application of the sensing apparatus is an apparatus for detecting engine oil quality change in an engine system. With the sensing apparatus, a first aging factor can be calculated after an engine cold soak and a second one can be obtained during engine operation. With these two aging factors, in addition to oil quality change, failures in the engine system and sensors, and oil change events can also be detected. Additionally, since reference sensing values are provided by the reference sensor, power disconnections have least effects.

20 Claims, 11 Drawing Sheets

FLUID QUALITY SENSING MEANS WITH REFERENCE SENSOR

This present application claims priority from U.S. provisional application No. 61/701,494 having the same title as the present invention and filed on Sep. 14, 2012.

CROSS-REFERENCE TO RELATED APPLICATIONS

Not applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

FIELD OF THE INVENTION

This invention relates to a method and apparatus for electrical measurement of a quality of a fluid in a fluid system, and more particularly to a method and apparatus using impedance of a fluid to detect changes in fluid quality and issues in a fluid system.

BACKGROUND OF THE INVENTION

In a fluid system, to have an adequate fluid replacement maintenance schedule for minimizing maintenance costs and system downtime, and to detect changes in fluid properties and issues in the fluid system, fluid quality needs to be monitored. One example of such a fluid system is an internal combustion engine system, in which engine oil is used for dissipating heat generated by friction of mechanical components and lubricating the movement of the mechanical components. During engine operations, soot particles and water generated in fuel combustion, water in ambient environment, water and glycols in engine coolant, metallic particles produced in the movement of pistons in cylinders, and fuel released in post-injections (in diesel engines) may enter the engine oil, dissolved or suspended therein. In addition, some oil additives, such as viscosity improvers and anti-oxidants breaks down during engine operation, especially at high temperature and in the presence of water and metallic particles, making the engine oil more acidic.

When the engine oil deteriorates to a certain level, it must be replaced. However, too frequent replacement of the engine oil increases the down time and operation cost of the engine, while if the engine oil exceeds its useful life, the engine could be damaged. To have an appropriate maintenance schedule, a condition-based maintenance is used, in which engine oil maintenance is based on knowledge of oil deterioration status, e.g., the difference between fresh oil and aged oil, and an oil quality sensor is used for detecting the oil deteriorations status.

In addition to facilitating the engine oil maintenance, some advanced engine control strategies, such as cam phasing VVT, variable displacement, and two-step valve actuation also require having knowledge of oil status, e.g., oil quality status and oil change events, to adaptively adjust controls. And to avoid sensor issues from causing control failures, the detection of issues in the oil quality sensors is required. Furthermore, in the engine oil system, oil quality sensors can also be used to detect failures in other components, such as oil filters. For example, when an oil filter lost its capability in removing debris in the engine oil, the concentration of contaminants would rise rapidly, causing a sudden change in the sensing values obtained from the oil quality sensors. Thereby by using changing rate the sensing values, oil filter failures can be detected.

A variety of sensing technologies can be used for detecting changes in fluid quality. For example, U.S. Pat. No. 6,459,995 describes an oil quality sensing apparatus based on permittivity measurement. In U.S. Pat. No. 7,504,835, a method for measuring impedance of an oil quality sensor is disclosed. An oil viscosity sensing means is described in U.S. Pat. No. 8,127,597. However, in examining fluid quality, it is difficult to determine a reference value to compare with due to the sensitivity to fluid types. For example, in impedance sensing, the impedance obtained from a capacitive sensor changes with fluid type, fluid temperature, and impurities in fluid, which the sensor is used to detect. The effect of fluid temperature can be compensated by using a temperature sensor, while that of fluid type is difficult to compensate, since the sensing for fluid type itself needs a quality sensor, and fluid quality changes with time.

To exclude the effect of fluid type in obtaining a reference value, a method is using a memory to store sensing values obtained from different fluids and identify the fluid type in a measurement (e.g. a method disclosed in U.S. Pat. No. 6,459, 995). Theoretically, after a fluid type is identified, the effect of fluid type can be compensated. However, in practice, normally it is difficult to measure all available fluids, since in addition to large number of fluid types, a new fluid can be easily created by mixing different type of fluids. Furthermore, due to the effects of impurity and temperature, the moment for the identification is difficult to determine, and the content saved in memory may be lost in applications with power disconnected after operations.

Fluid change events normally cannot be detected by using a fluid quality sensor due to the difficulties in distinguishing sensing value changes caused by a fluid change event and a fluid failure. However, using other means for detecting fluid change may have issues. For example, in an engine system, a commonly used method for detecting oil change is using a switch button. When engine oil is changed, the operator needs to press the switch button to change a signal state which is then detected by an ECU (Engine Control Unit) as an indication of oil change. If the operator forgets to press the button or mistakenly presses the button, a false oil change event is detected. Using a fluid level sensor is able to automatically detect a fluid change. However, both of fluid slosh and tiltedly positioned fluid container create issues to the detection.

When sensing values obtained from fluid quality sensors are used in system controls, sensor failures may cause problems in the fluid system. For example, when oil quality is used in the variable displacement control of an engine system, false sensing values may create control and OBD issues. To avoid these problems from happening, sensor rationality needs to be examined. The rationality examination for a quality sensor is challenging since the sensing value obtained from the quality sensor needs to be compared with an independent sensing value, and it is difficult to have the independent sensing value.

To have a reliable reference value for examining fluid quality, it is then an objective of the present invention to provide a reference sensing means that is able to generate a reference sensing value for a fluid quality sensor. The reference sensing value is obtained for a reference fluid the same type as a system fluid sensed by the fluid quality sensor, and the reference fluid is automatically refreshed to the system fluid during a fluid change.

A further objective of the present invention is to provide a reliable sensing means and method using fluid quality sensors to automatically detect fluid change events. This sensing means and method is able to distinguish fluid change events from fluid failures and at the same time is insensitive to fluid slosh and the inclination angle of a fluid container.

Yet another objective of the present invention is to provide a reliable sensing means least affected by power disconnections.

Yet another objective of the present invention is to provide a method for detecting sensor rationality issues in a fluid quality sensing means including a reference sensor and a fluid quality sensor.

Yet another objective of the present invention is to provide a method for detecting changes in fluid quality using impedance obtained from a capacitive reference sensor and a capacitive fluid quality sensor.

BRIEF SUMMARY OF THE INVENTION

The present invention provides apparatus for detecting changes in fluid quality using signals obtained from a fluid quality sensor for exposure to a fluid in a fluid system and a reference sensor positioned in a reference sensing means holding a reference fluid, which is part of the fluid in the fluid system.

In accordance with an exemplary embodiment of the present invention, a fluid quality sensor is installed inside a fluid system with an inlet port, and a reference sensor is positioned in a reference sensing means including a fluid trap section, which has an inlet section fluidly connected to the inlet port of a fluid tank, a "U" shape fluid trap section holding part of the fluid when it is refilled into the fluid tank, and an outlet section. During the operation of the fluid system, since the fluid trapped in the reference sensing means is isolated from the fluid in the fluid system, it is not affected. Therefore, the difference between the sensing values obtained from the fluid quality sensor and the reference sensor provides an indication of the deterioration of the fluid in the fluid system. Furthermore, since the trapped fluid is refreshed every time the fluid is refilled, it is with the same type as that in the fluid system.

Preferably the fluid quality sensor and the reference sensor are capacitive sensors and sensing values are impedance values obtained from the sensors. And a temperature sensor can be integrated with the capacitive sensors for providing fluid temperature information in compensating the sensing values. In the present invention, an aging factor is calculated with the impedance values obtained from the fluid quality sensor and the reference sensor. An exemplary method for determining the aging factor is calculating the distance between the impedance values, which are, respectively, the ones with the maximum magnitude among all measured values at different frequencies obtained from the fluid quality sensor and the reference sensor. The aging factor can also be calculated using a sum of weighted distance between the impedance of the fluid quality sensor and the reference sensor obtained at each measured frequency. Another exemplary method is calculating the change in the dielectric dissipation factor using the real parts of the impedance values.

An application of the sensing apparatus is to detect oil deterioration in an internal combustion engine. In accordance with an exemplary embodiment of the application, the sensing apparatus with an oil quality sensor installed in an oil tank and a reference sensor in a reference sensing means is used after a long time engine shutdown, i.e., a cold sock, for providing an aging factor value of the oil. The cold sock is to decrease the temperature difference between the trapped oil in the reference sensing means and the oil in the oil tank. In accordance with another exemplary embodiment of the application, a second aging factor value is calculated by using the impedance sensing values obtained from the oil quality sensor during engine operation. One of the impedance sensing value is obtained right after key-on of the engine, and the comparison between the impedance sensing values provides an indication of oil deterioration during engine operation. In addition to oil quality, the second aging factor together with the first one obtained after a cold sock can be further be used for detecting oil change events and sensor issues.

DETAILED DESCRIPTION OF THE INVENTION

Figure 1:
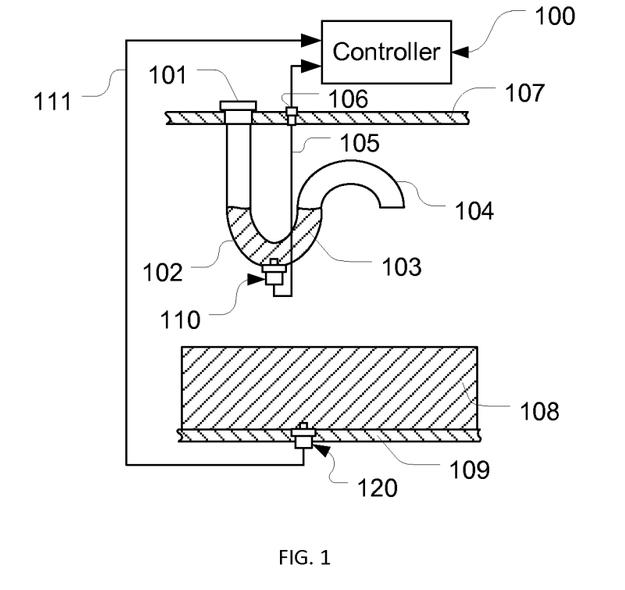
FIG. 1 is a diagrammatic illustration of a fluid system with a fluid quality sensor and a reference sensing means.

Referring to FIG. 1, a fluid quality sensor 120 is mounted on a bottom wall 109 of a fluid tank (not shown) contacting a fluid 108. On a top wall 107 of the fluid tank, a cap 101 is positioned on the inlet of an "S" shape tube with a "U" shape trap section 102 and an outlet section 104. On the bottom of the trap section 102, a reference fluid quality sensor 110 is mounted, contacting trapped fluid 103 in the trap section 102. The fluid quality sensor 120 is electrically connected to a controller 100 with signal lines 111, while the reference fluid quality sensor 110 is electrically connected to the controller 100 with signal lines 105 via a port 106 on the top wall 107.

When a fluid is refilled into the fluid tank, new fluid is trapped in the trap section 102. The trapped fluid is isolated from rest of the fluid, therefore, its quality doesn't change with fluid usage. The fluid quality of the trapped fluid in the trap section 102 and that of the aged fluid in the fluid tank are measured by the fluid quality sensor 120 and the reference sensor 110 respectively. By comparing the measured values, the quality change of the fluid in the fluid tank is then detected.

Figure 2A:
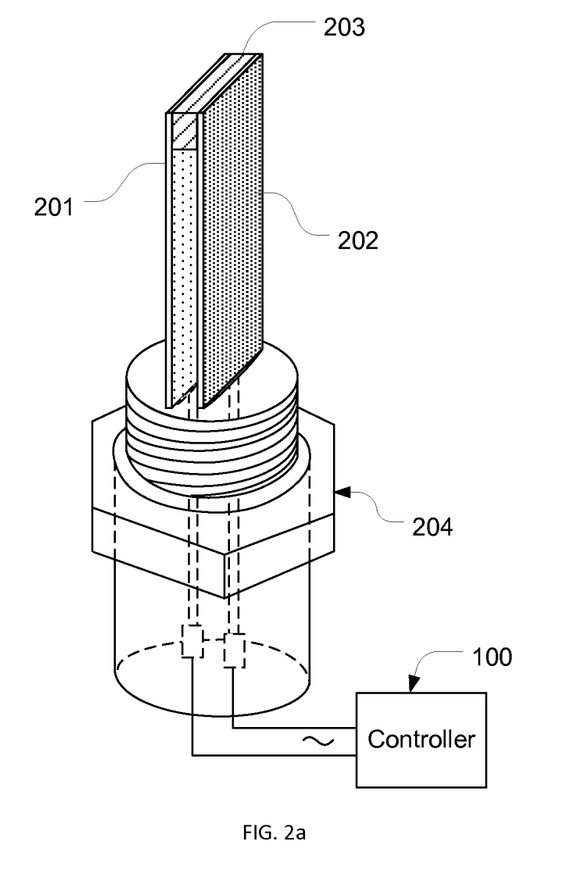
FIG. 2a is a diagrammatic illustration of a capacitive fluid quality sensor with two parallel electrode pads.
Figure 2B:
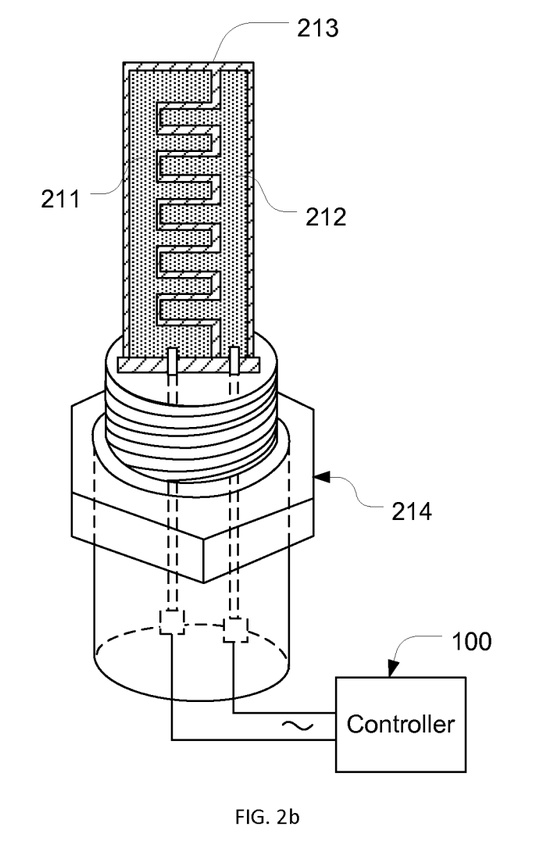
FIG. 2b is a diagrammatic illustration of a capacitive fluid quality sensor with a pair of comb electrodes.

A variety types of sensors, including but not limited to capacitive sensors, inductive sensors, and resistive sensors, can be used as the fluid quality sensors 110 and 120. In an exemplary application of this device, the fluid is oil in an internal combustion engine, and the fluid quality sensors 110 and 120 are capacitive sensors. Referring to FIG. 2a, a capacitive sensor including two parallel electrode plates 201 and 202 can be used as the fluid quality sensors 110 and 120. The two electrode plates 201 and 202 are positioned on a sensor connector 204 and electrically connected to the controller 100. A nonconductive separator 203 on the top end of the electrode plates 201 and 202 is used to support and separates the two electrode plates. A comb capacitive sensor as shown in FIG. 2b an also be used for the fluid quality sensors 110 and 120. In this sensor, two comb electrodes 211 and 212 are mounted on a flat base 213, which is nonconductive, and the sensing piece is installed on a sensor connector 214. In addition to the ones shown in FIGS. 2a and 2b, other types of electrodes, such as concentric rings and coaxial cylinders can also be used. There is no intent to restrict the geometry of the electrodes in the present invention.

Figure 2C:
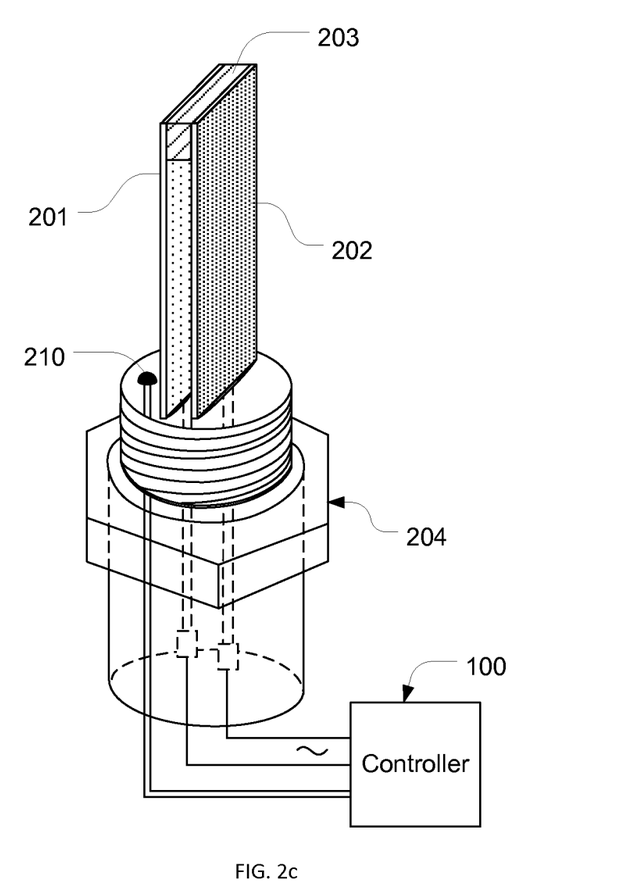
FIG. 2c is a diagrammatic illustration of a capacitive fluid quality sensor with a temperature sensor.

In a fluid, impedance measured with the capacitive electrodes is a function of fluid type, the impurity level in the fluid, and the temperature of the fluid. To exclude the effects of fluid temperature, a temperature sensor can be integrated together with the capacitive sensor so that the impedance values obtained from the capacitive sensor can be compensated with the fluid temperature. An integrated fluid quality sensor is shown in FIG. 2c. In this sensor, a temperature sensor 210 is positioned on the sensor connector 204 together with the two electrodes 201 and 202. And the temperature sensor 210 is electrically connected to the controller 100.

Figure 3:
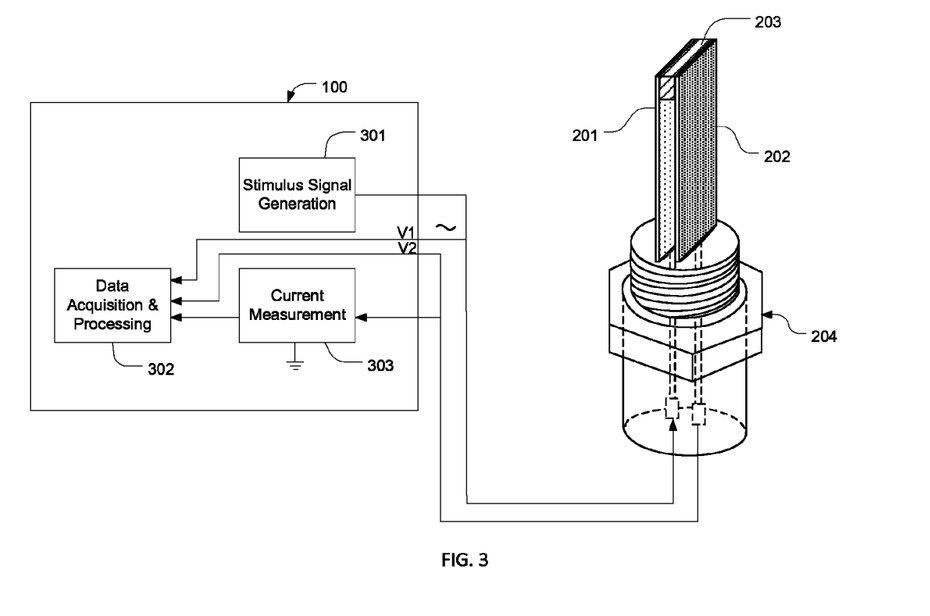
FIG. 3 shows an exemplary circuit for obtaining sensing values from a capacitive sensor.

A variety of circuits can be used for measuring the impedance of the capacitive sensor in the controller 100. An example of such a circuit is shown in FIG. 3. In this circuit, a stimulus signal generation block 301 generates an alternate stimulus signal V1 and applies it to the electrode 201 of the capacitive sensor. The stimulus signal V1 is also provided to a data acquisition and processing block 302 together with a voltage signal V2 at the electrode 202. The other electrode 202 of the capacitive sensor is connected to a current measurement block 303, with which the alternate current passing through the electrodes 201 and 202 is converted to a current sensing signal to the data acquisition and processing block 302. The voltage signals and the current sensing signal are then used in calculating the impedance of the capacitive sensor. To avoid redox reactions on the surface of the electrodes 201 and 202 and polarization of the electrodes, the amplitude of the stimulus signal should be kept small and an alternate stimulus signal is preferred.

Referring back to FIG. 1, with the capacitive quality sensors 110 and 120, in an exemplary application of an engine lubrication system, the cap 101 is an oil filler cap, and oil is added in the system through the cap 101, the "S" shape tube with a "U" shape trap section 102 and an outlet section 104. The bottom wall 109 is a bottom wall of an oil sump. After an oil refill, part of the refilled oil 103 remains in the trap section 102, and rest of the refilled oil enters the engine lubrication system, cycling in it. The trapped oil 103 is isolated from rest of the engine lubrication system. Therefore, its quality doesn't change with the oil 108 in the oil sump, and the difference in the impedance obtained from the quality sensors 110 and 120 reflects the condition of the oil 108.

If the temperature of the oil 108 or the oil 103 is not available, then in determining the condition of the oil 108, the impedance of the quality sensors 110 and 120 should be obtained under the same temperature to avoid effects of the temperature difference. In the application of the engine lubrication system, a cold soak of the engine, i.e., a long off-time of the engine, can be used to determine the temperature condition. And an exemplary algorithm for determining the cold soak and calculating an oil aging factor with the impedance obtained from the quality sensors can be realized with a service routine running periodically for a timer based interrupt.

Figure 4:
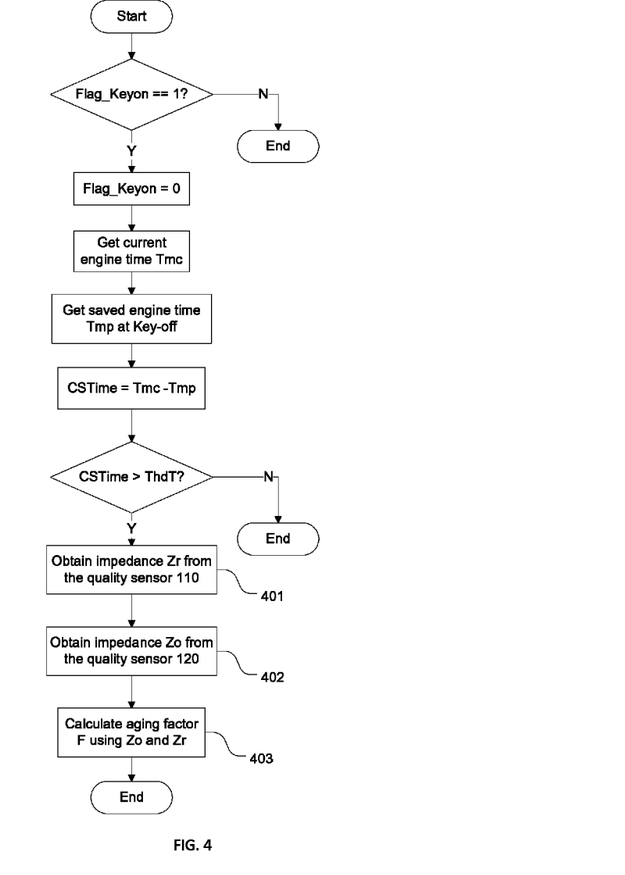
FIG. 4 is a flowchart of an exemplary service routine for a timer based interrupt running periodically for calculating an aging factor with impedance sensing values obtained from a fluid quality sensor and a reference sensor.

Referring to FIG. 4, when the routine starts, it examines the value of a flag Flag_Keyon, which is set upon a rising edge of a key switch signal. If the flag Flag_Keyon is not set, then the routine ends, otherwise, the flag Flag_Keyon is reset to 0, and a current engine time Tmc is compared with an engine key-off time Tmp, which is saved at the last key-off. If the difference between the current engine time Tmc, and the key-off time Tmp is longer than a threshold ThdT, then a cold soak is detected, otherwise, the routine ends. Upon the cold soak, a reference impedance Zr is obtained from the quality sensor 110 in a step 401, and an oil impedance Zo is obtained from the quality sensor 120 in a step 402. Before the routine ends, in a step 403, an aging factor F is calculated with the impedance Zr and Zo.

In the steps 401 and 402, a variety of methods can be used in obtaining the impedance Zo and Zr. One method is a transfer function method. In this method, the stimulus signal V1 (FIG. 3) is a broadband signal applied on one electrode of the quality sensors 110 and 120. Then the voltage signal V2 is generated at another electrode together with a current sensing signal, Isn. When a Fourier transform is applied, the values of the signals V1, V2, and Isn become $V1(\omega)$, $V2(\omega)$, and $Isn(\omega)$ respectively. And the impedance Z of the quality sensors can be calculated therewith using the following equation:

$$Z=(V1(\omega)-V2(\omega))/Isn(\omega). \quad (1)$$

Ideally, the impedance Z is the oil impedance. However, the sensor itself may have intrinsic impedance Zi, which is the impedance of the capacitive sensor when the sensing electrodes (e.g. the electrodes 201 and 202 in FIG. 2a, and the electrodes 211 and 212 in FIG. 2b) are short-circuited. This intrinsic impedance may be caused by inductance, capacitance, and resistance of the wires, probe, and signal processing circuits, and signal propagation delay. To eliminate the effects of the intrinsic impedance, the intrinsic impedance needs to be excluded from the measured impedance:

$$Z=(V1(\omega)-V2(\omega))/Isn(\omega)-Zi. \quad (2)$$

The impedance Zo and Zr can be calculated using either equation (1) or equation (2), depending on the effects of the intrinsic impedance Zi and the measurement requirements.

Another method for measuring the impedance of the quality sensors is a single frequency method applying a sine wave stimulus signal at an interested frequency, $V1(\omega t)$, on one electrode of the capacitive quality sensors, and measuring the voltage $V2(\omega t-\phi)$ on the other electrode and the current Isn $(\omega t-\phi)$ passing through the electrodes, where $\phi$ is the phase shift of the signal. The impedance can then be calculated using the following equation:

$$Z=[(|V1(\omega t)|-|V2(\omega t-\phi)|)/|Isn(\omega t-\phi)|](\cos\phi+j\sin\phi), \quad (3)$$

where j is the square root of −1. As mentioned above, to increase measurement accuracy, in calculating the measured impedance, the intrinsic impedance Zi needs to be deducted from the value calculated in equation (3):

$$Z=[(|V1(\omega t)|-|V2(\omega t-\phi)|)/|Isn(\omega t-\phi)|](\cos\phi+j\sin\phi)-Zi. \quad (4)$$

In the step 403, the aging factor F is an indication of oil deterioration. It can be calculated using the impedance Zo and Zr with a number of methods. One simple method is calculating the distance between the impedance Zo and Zr using the values with the maximum magnitude among all measured values obtained at different frequencies. In this method, if $Zo(\omega_{om})$ and $Zr(\omega_{rm})$ are, respectively, the values of the impedance Zo and Zr with the maximum magnitude, then we have $$Zo(\omega_{om})=Zom\{Re\}+jZom\{Im\}, \quad (5)$$

and $Mag(Zo(\omega_{om}))=\max(Mag(Zo(\omega_i)))$, i=1, 2, ..., n), where n is the number of measurement frequencies; $Zom\{Re\}$ and $Zom\{Im\}$ are the real part and the imaginary part of the impedance value $Zom(\omega_{om})$ respectively, and "Mag" is an abbreviation denoting magnitude;

$$Zr(\omega_{om})=Zrm\{Re\}+jZrm\{Im\}, \quad (6)$$

and $Mag(Zr(\omega_{rm}))=\max(Mag(Zr(\omega_i)))$, i=1, 2, ..., n), where $Zrm\{Re\}$ and $Zrm\{Im\}$ are the real part and imaginary part of the impedance value $Zrm(\omega_{rm})$ respectively. The aging factor F is then calculated using the following equation:

$$F=\mathrm{sqrt}((Zom\{Re\}-Zrm\{Re\})^2+(Zom\{Im\}-Zrm\{Im\})^2), \quad (7)$$

where "sqrt" an abbreviation denoting square root.

In addition to the above method, another distance calculation method is calculating a sum of weighted distance between the impedance Zo and Zr at each measured frequency. In this method, the aging factor F can be calculated using the following equation:

$$F=\mathrm{sum}(\mathrm{sqrt}((Zo\omega i\{Re\}-Zr\omega i\{Re\})^2+(Zo\omega i\{Im\}-Zr\omega i\{Im\})^2)Wi, i=1,2,\ldots n), \quad (8)$$

where $Zo\omega i$ and $Zr\omega i$ are the values of impedance Zo and Zr obtained at a frequency $\omega_i$; Wi is the weighing factor number for the frequency $\omega_i$. According to equation (8), since the real part and the imaginary part of the impedance $Zr\omega i$ are deducted from the impedance $Zo\omega i$, if the same type of capacitive sensors are used for the quality sensors 110 and 120, then the impedance can be measured according to equations (1) and (3), since the effects of sensor intrinsic impedance are canceled out in the calculation.

When the impedances Zo and Zr are measured at a single frequency and the same type of capacitive sensors are used for the quality sensors 110 and 120 (FIG. 1), the change in the dielectric dissipation factors of the capacitive sensors can be used as the aging factor F. In this calculation, assuming the capacitance of the sensors 110 and 120 are, respectively, Co and Cr. Then, the impedances Zo and Zr are respectively:

$$Zo=1/(j\omega Co)=1/(j\omega Ci(1-j\mathrm{Tan}(\delta o)))=1/(\omega Ci\mathrm{Tan}(\delta o)+j\omega Ci), \quad (9)$$

and $$Zr=1/(j\omega Cr)=1/(j\omega Ci(1-j\mathrm{Tan}(\delta r)))=1/(\omega Ci\mathrm{Tan}(\delta r)+j\omega Ci), \quad (10)$$

where $\mathrm{Tan}(\delta o)$ and $\mathrm{Tan}(\delta r)$ are, respectively, the dielectric dissipation factors of the capacitors Co and Cr, and Ci is the capacitance with lossless dielectric. According to equations (9) and (10), the aging factor F can be calculated using the following equation:

$$F=(\mathrm{Real}(1/Zo)-\mathrm{Real}(1/Zr))/\mathrm{Real}(1/Zr)=(\mathrm{Tan}(\delta o)-\mathrm{Tan}(\delta r))/\mathrm{Tan}(\delta r), \quad (11)$$

where $\mathrm{Real}(1/Zr)$ is the real part of the 1/Zr value, and Real(1/Zo) is the real part of the 1/Zo value. The aging factor F calculated in equation (10) is then the relative change in the dielectric dissipation factor of the oil quality sensor 120 with reference to the reference sensor 110.

In addition to the impedance obtained from the oil quality sensor 120 and the reference sensor 110 after a cold soak, the impedance of the oil quality sensor 120 obtained at an operating temperature of the oil can also be used for detecting oil quality change. According to equation (11), when the Zr value is replaced with a Zo1 value, which is the impedance of the sensor 120 obtained at a temperature Th at a moment t1, and the Zo value is replaced with an impedance value Zo2 obtained from the sensor 120 at the same temperature Th at another moment t2, then the calculated aging factor value, $\Delta$Fh, indicates the oil quality change during the time period from the moments t1 to t2:

$$\Delta Fh=(\mathrm{Real}(1/Zo2)-\mathrm{Real}(1/Zo1))/\mathrm{Real}(1/Zo1). \quad (12)$$

Figure 5:
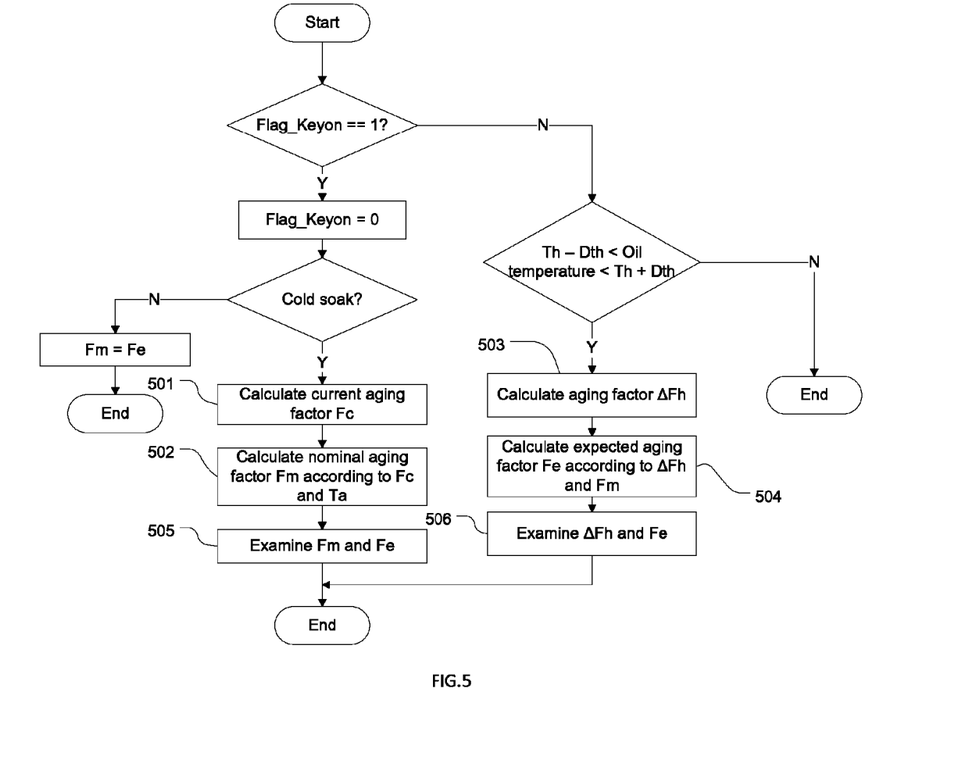
FIG. 5 is a flowchart of an exemplary service routine for a timer based interrupt running periodically for examining fluid quality sensing values obtained from an oil quality sensor and a reference sensor.

With the aging factor values calculated according to equations (11) and (12), the oil quality sensor 120 and the reference sensor 110 can be used for detecting failures in the oil and sensors. An exemplary algorithm for the detections is realized with a service routine, as shown in FIG. 5, running periodically for a timer based interrupt. This routine starts with examining the value of the flag Flag_Keyon. When it is 1, the flag Flag_Keyon is set to 0, and then cold soak is examined using the method of FIG. 4. If there is no cold soak before the key-on, then the value of an expected aging factor Fe is assigned to a nominal aging factor Fm, and routine ends. Otherwise, a current aging factor Fc is calculated in a step 501. In a step 502, the nominal aging factor Fm is calculated with the current aging factor Fc and a measured ambient temperature Ta, and after examining the nominal aging factor Fm and the expected aging factor Fe, the routine ends. Referring back to the examination of the flag Flag_Keyon, if it is 0, then the oil temperature is compared with two thresholds, Th−Dth and Th+Dth. The routine ends if the oil temperature is not within the range bounded by these two thresholds, otherwise, in a step 503, the aging factor $\Delta$Fh is calculated and in a step 504, the expected aging factor Fe is calculated according to the $\Delta$Fh value and the Fm value. The routine ends after the $\Delta$Fh value and the Fe value being examined in a step 506.

In the step 501, the current aging factor Fc can be calculated using an interrupt service routine of FIG. 4. And the impedance of the oil quality sensor 120 and the reference sensor 110 under the ambient temperature Ta, Zo(Ta) and Zr(Ta), are obtained in the calculation as well. The value of the current aging factor Fc under the ambient temperature Ta is then converted into the nominal value Fm in the step 502. The conversion is to calculate the aging factor value at a nominal temperature using the values of Fc and Ta according to the relation between aging factor and temperature. A lookup table can be used in the calculation, and the lookup table can be populated using test results obtained from a test with different aging factor and temperature settings. The Fm value is also used in the step 504 for calculating the expected aging factor Fe, together with the aging factor in the current key cycle, $\Delta$Fh, calculated in the step 503 according to equation (12). In calculating the $\Delta$Fh value, the impedance Zo1 can be either the impedance measured at the first moment at which the oil temperature reaches the Th value, or an impedance converted from the Zo(Ta) value obtained in the step 501 at key-on. A lookup table with inputs of impedance and temperature can be used in converting the Zo(Ta) value.

Figure 6A:
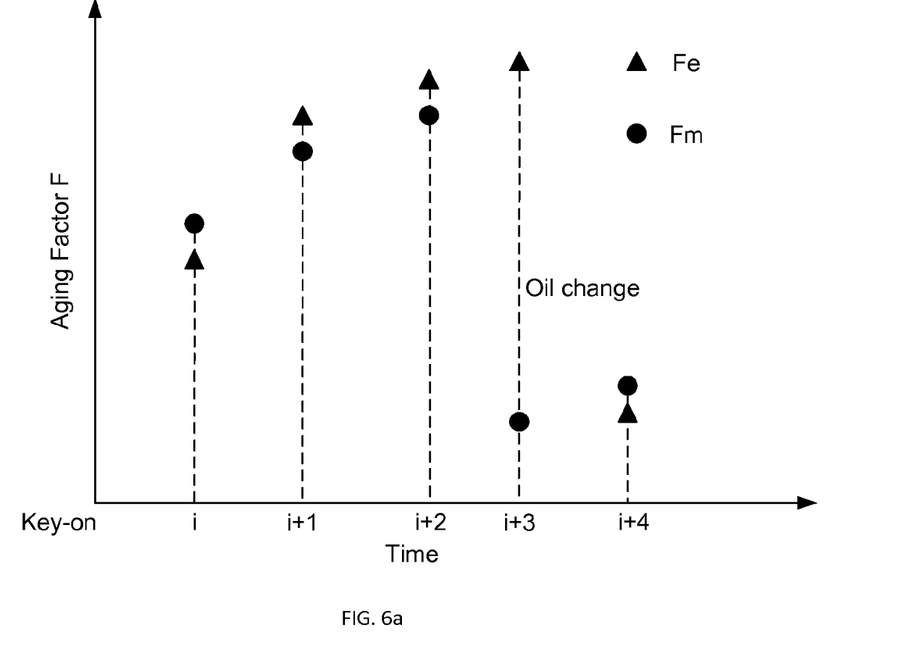
FIG. 6a is a timing chart of the examination in the step 505 of FIG. 5 for detecting an oil change event.
Figure 6B:
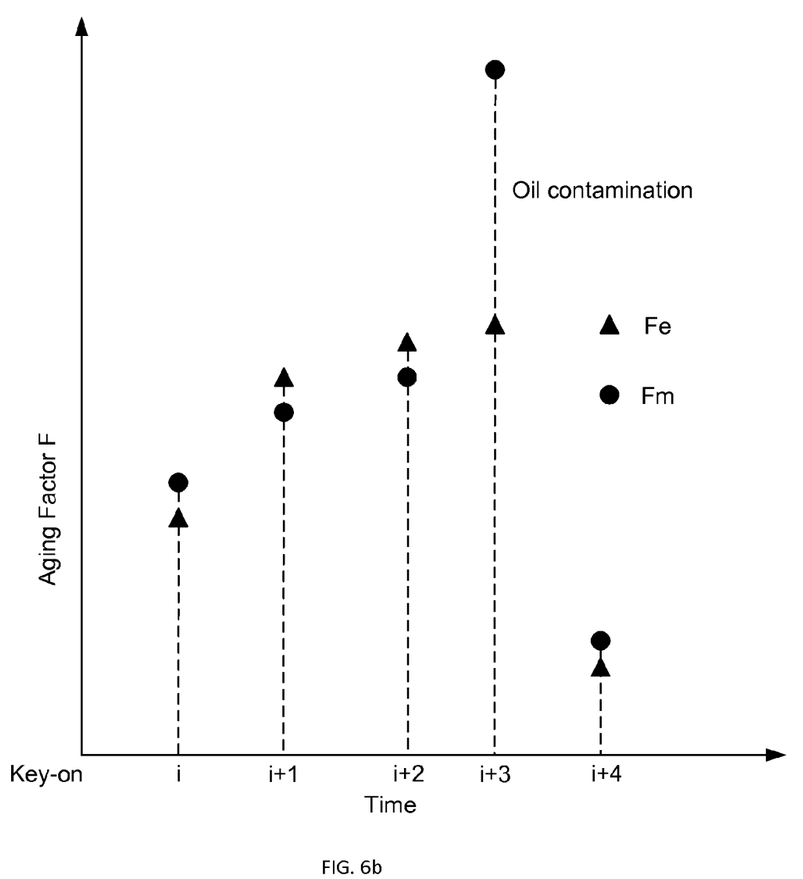
FIG. 6b is a timing chart of the examination in the step 505 of FIG. 5 for detecting an oil contamination.

In the step 504, a simple method for calculating the expected factor Fe is converting the $\Delta$Fh value to an aging factor value at the nominal temperature, $\Delta$Fhm, and then adding the Fm value to it. The Fm value and the Fe value saved right before the last key-off are then examined in the step 505. And an oil change event or oil contamination can be detected by the examination. Referring to FIG. 6a and FIG. 6b, in which the black dots denote the Fm values, and the black triangles are the Fe values, if there is no change in the oil, then since there is no engine operation during key-off, the Fm values should be close to the Fe values right after a key-on (e.g. the ith, (i+1)th, (i+2)th, and (i+4)th key-ons). If the oil in the tank is replaced during key-off, then since the oil quality sensor 120 and the reference sensor 110 are positioned in the same oil after the oil change, as shown in FIG. 6a, the Fm value decreases significantly causing a mismatch to the Fe value at the (i+3) key-on. If the Fm value calculated at key-on is significantly higher than the Fe value, then as shown in the (i+3)th key-on in FIG. 6b, the oil is contaminated.

Figure 7A:
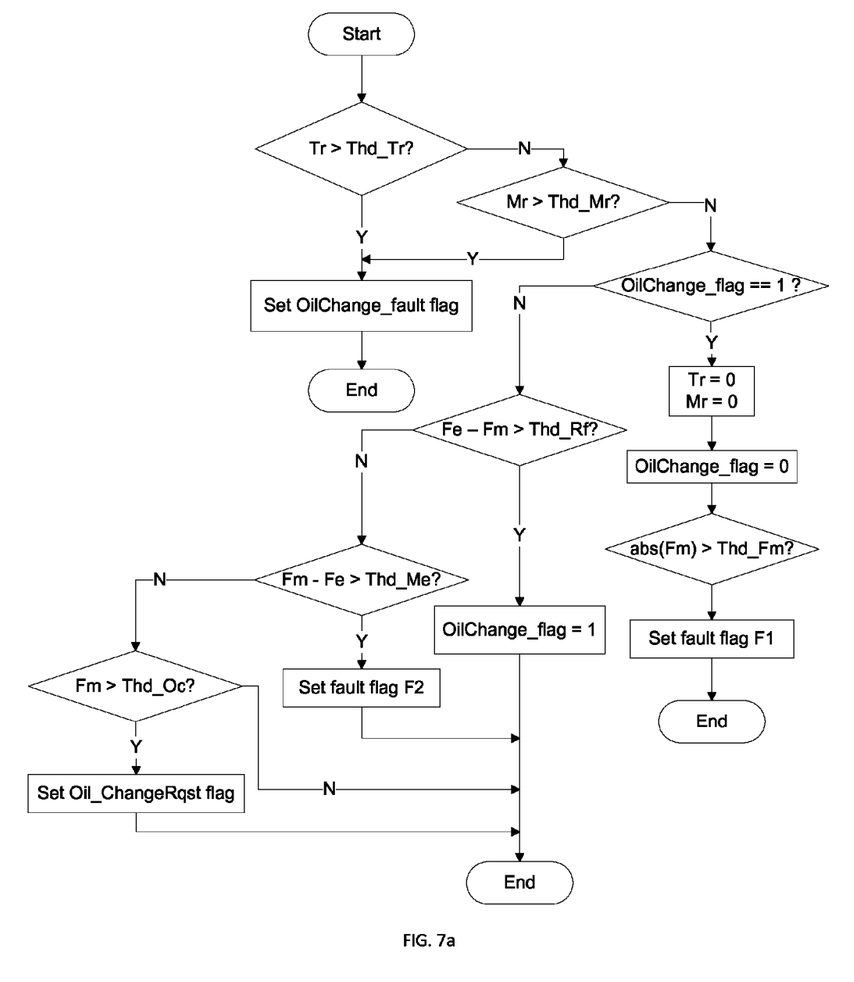
FIG. 7a is a flowchart of an exemplary implementation for the step 505 of FIG. 5.

The examination for the Fe and Fm values in the step 505 can be realized with a service routine running periodically for a timer based interrupt. Referring to FIG. 7a, when the routine starts, a time interval variable Tr, which is the time since the last oil change, and a mileage variable Mr, which is the vehicle mileage since the last oil change, are examined. If the Tr value is higher than a threshold Thd_Tr, or the Mr value is higher than a threshold Thd_Mr, then a fault flag OilChange_fault is set, and the routine ends, otherwise, the value of a flag, OilChange_flag, is checked. If it is 1, i.e., an oil change event is detected, then the Tr and Mr values are reset to 0. After the flag OilChange_flag is reset to 0, the absolute value of Fm is compared to a threshold Thd_Fm. If it is higher than the threshold, then a fault flag F1 is set and the routine ends. The fault F1 is an indication of sensor failures, since the value of the aging factor Fm should be very small right after an oil change. Referring back to the examination of the Oil-Change_flag value, if it is not 1, then the difference between the values of Fe and Fm is compared to a threshold Thd_Rf. When the Fe value is higher the Fm value and the difference is higher than the threshold, then an oil change is detected, and the routine ends after the OilChange_flag value is set to 1, otherwise, the difference is compared to another threshold Thd_Me. If the Fe value is lower than the Fm value, and the difference is higher than the threshold Thd_Me, then a fault flag F2 is set and the routine ends, otherwise, the Fm value is compared to a threshold Thd_Oc. Before the routine ends, if the Fm value is higher than the threshold Thd_Oc, then an oil change is needed, and a flag Oil_ChangeRqst flag is set to 1. The fault flag F2 is an indication of oil contamination.

Figure 7B:
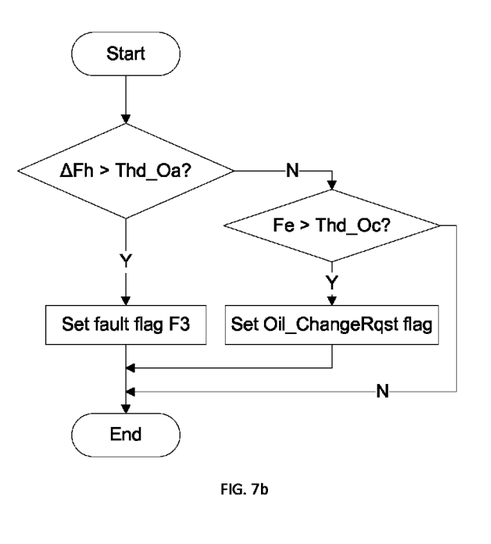
FIG. 7b is flowchart of an exemplary implementation for the step 506 of FIG.

The values of Fe and ΔFh are also examined in the step 506, and a service routine running periodically for a timer based interrupt can be used for the examination. Referring to FIG. 7b, after the routine starts, the ΔFh value is compared to a threshold Thd_Oa first. If it is higher than the threshold, then a fault flag F3 is set, and the routine ends. The fault flag F3 is an indication of an engine failure that causes quick contamination of the oil, for example, a gasket failure in the engine causes coolant mix with engine oil. If the ΔFh is not higher than the threshold Thd_Oa, then the Fe value is compared to a threshold Thd_Oc. If it is higher than the threshold, then an oil change is needed, and a flag Oil_ChangeRqst flag is set. The routine ends thereafter.

Although the apparatus and method of the invention are described herein in relation to the preferred embodiments shown in FIGS. 1-7, certain design alternations and modifications will become apparent to those of ordinary skill in the art upon reading this disclosure in connection with the accompanying drawings. It is intended, however, that the scope of the invention be limited only by the appended claims.

What is claimed is:

1. An apparatus for measuring fluid quality and degradation in a fluid system, comprising:
    a fluid container containing a system fluid being used in said fluid system;
    a fluid filler passage fluidly connected to said fluid container for said system fluid to flow therethrough during a refill process including a fluid trap section holding a portion of said system fluid being refilled in said refill process as a reference fluid;
    a first sensor generating a first sensing signal indicative of at least one property of said reference fluid being held in said fluid trap section;
    a second sensor generating a second sensing signal indicative of said at least one property of said system fluid in said fluid container; and
    a controller configured to generate a fluid quality signal indicative of a quality of said system fluid in response to said first sensing signal and said second sensing signal.

2. The apparatus of claim 1, wherein said fluid trap section includes a U-shaped fluid passage with one end fluidly connected to said fluid container.

3. The apparatus of claim 1, wherein said first sensing signal is indicative of an impedance of said first sensor and said second sensing signal is indicative of an impedance of said second sensor.

4. The apparatus of claim 3, wherein said first sensor and said second sensor are capacitive sensors.

5. The apparatus of claim 3, further comprising:
    a temperature sensor generating a temperature sensing signal indicative of a temperature of said reference fluid being held in said fluid trap section.

6. The apparatus of claim 3, further comprising:
    a temperature sensor generating a temperature sensing signal indicative of a temperature of said system fluid in said fluid container.

7. The apparatus of claim 1, wherein said controller is further configured to generate said fluid quality signal when a difference between a temperature of said reference fluid held in said fluid trap section and a temperature of said system fluid in said fluid container is within a predetermined range.

8. An oil quality diagnostic system of an internal combustion engine, comprising:
    an oil container containing an engine oil being used in said internal combustion engine;
    an oil filler passage fluidly connected to said oil container for said engine oil to flow therethrough during a refill process including an oil trap section holding a portion of said oil being refilled in said refill process as a reference oil;
    a first sensor generating a first sensing signal indicative of at least one property of said reference oil being held in said oil trap section;
    a second sensor generating a second sensing signal indicative of said at least one property of said engine oil in said oil container; and
    a diagnostic controller adapted to:
        determine a first aging factor value in response to said first sensing signal and said second sensing signal; and
        identify a first fault when said first aging factor value is higher than a predetermined threshold.

9. The oil quality diagnostic system of claim 8, wherein said fluid trap section includes a U-shaped fluid passage with one end fluidly connected to said oil container.

10. The oil quality diagnostic system of claim 8, wherein said first sensing signal is indicative of an impedance of said first sensor and said second sensing signal is indicative of an impedance of said second sensor.

11. The oil quality diagnostic system of claim 8, wherein said diagnostic controller is further adapted to determine said first aging factor value after said internal combustion engine is turned off for a period of time longer than a predetermined threshold.

12. The oil quality diagnostic system of claim 8, wherein said diagnostic controller is further adapted to determine a second aging factor value in response to said second sensing signal.

13. The oil quality diagnostic system of claim 12, wherein said diagnostic controller is further adapted to:
   determine a first sensing value in response to said second sensing signal at a first moment;
   determine a second sensing value in response to said second sensing signal at a second moment; and
   determine said second aging factor value in response to at least said first sensing value and said second sensing value.

14. The oil quality diagnostic system of claim 12, wherein said diagnostic controller is further adapted to identify a second fault when said second aging factor value is higher than a predetermined value.

15. The oil quality diagnostic system of claim 12, wherein said diagnostic controller is further adapted to determine a third aging factor value in response to said first aging factor value and said second aging factor value.

16. The oil quality diagnostic system of claim 15, wherein said diagnostic controller is further adapted to determine a third fault when said first aging factor value is higher than said third aging factor value and a difference between said first aging factor value and said third aging factor value is higher than a predetermined value.

17. The oil quality diagnostic system of claim 15, wherein said diagnostic controller is further adapted to identify an oil change event when said first aging factor value is lower than said third aging factor value and a difference between said first aging factor value and said third aging factor value is higher than a predetermined value.

18. A method for detecting a quality of a fluid in a fluid system including a fluid container containing a system fluid being used in said fluid system, a fluid filler passage fluidly connected to said fluid container for said system fluid to flow therethrough during a refill process including a fluid trap section, a first sensing piece positioned in said fluid trap section, and a second sensing piece positioned in said fluid container, comprising:
   storing a portion of said system fluid in said fluid trap section as a reference fluid;
   determining a first impedance value of said first sensing piece;
   determining a second impedance value of said second sensing piece;
   calculating real parts of said first impedance value and said second impedance value; and
   determining an aging factor value in response to said real parts of said first impedance value and said second impedance value.

19. The method of claim 18, further comprising:
   determining a first temperature value of said reference fluid in said fluid trap section and a second temperature value of said system fluid in said fluid container, wherein said aging factor value is determined only when a difference between said first temperature value and said second temperature value is lower than a predetermined value.

20. The method of claim 18, wherein said second sensing piece is the same type as said first sensing piece.

* * * * *